United States Patent [19]

Gilbert

[11] 4,141,239
[45] Feb. 27, 1979

[54] DEVICE AND KIT AND METHOD FOR MEASURING THE DEGREE OF DONENESS OF A COOKED PIECE OF MEAT

[76] Inventor: John E. Gilbert, 348 Washington St., Royersford, Pa. 19468

[21] Appl. No.: 907,037

[22] Filed: May 18, 1978

[51] Int. Cl.$^2$ .......................... G01N 3/42; G01N 3/48
[52] U.S. Cl. ................................. 73/81; 73/432 SD; 73/432 T; 99/342; 116/200; 116/205; 116/DIG. 17
[58] Field of Search .......... 73/81, 78, 432 SD, 432 T, 73/1 R; 116/114 G, 114 R, DIG. 17; 426/87; 99/342, 343

[56] References Cited

U.S. PATENT DOCUMENTS

| | | | |
|---|---|---|---|
| 2,296,815 | 9/1942 | Evans | 35/19 |
| 2,446,956 | 8/1948 | Ross | 73/81 |
| 2,652,718 | 9/1953 | Wiseman | 73/78 |
| 2,913,899 | 11/1959 | Wohler | 73/94 |
| 2,975,631 | 3/1961 | Hansen | 73/81 |
| 3,308,654 | 3/1967 | Badgley | 73/81 |
| 3,564,735 | 2/1971 | Fisher | 35/73 |
| 3,593,572 | 7/1971 | Hansen | 73/81 |
| 3,696,662 | 10/1972 | Foltz | 73/81 |
| 3,872,716 | 3/1975 | Hansen | 73/81 |
| 4,007,632 | 2/1977 | Segars | 73/78 |

Primary Examiner—S. Clement Swisher
Assistant Examiner—Denis E. Corr
Attorney, Agent, or Firm—Paul & Paul

[57] ABSTRACT

A plurality of blocks of resilient material are arrayed in proximity to each other. Each block has a predetermined amount of compressibility which is equal to the amount of compressibility of a model piece of meat which has been cooked to a known degree of doneness. In a preferred embodiment, four blocks will be labeled to indicate the corresponding degrees of doneness of four model pieces of meat which have been cooked to known degrees of doneness, and whose amounts of compressibility are equal to the amounts of compressibility of the blocks being labeled. In the preferred embodiment, the first block will be labeled rare, the second block medium rare, the third block medium well done and the fourth block well done. The degree of doneness of a cooked piece of meat can be measured by compressing the piece of meat and then compressing the blocks to determine which block has an amount of compressibility equal to the amount of compressibility of the cooked piece of meat. The degree of doneness of the cooked piece of meat will be the same as the degree of doneness of the model cooked piece of meat, which is correspondingly equal in amount of compressibility with the block, whose amount of compressibility equals that of the cooked piece of meat.

12 Claims, 3 Drawing Figures

DEVICE AND KIT AND METHOD FOR MEASURING THE DEGREE OF DONENESS OF A COOKED PIECE OF MEAT

BACKGROUND OF THE INVENTION

In the prior art possibly related to a device or kit or method of measuring the doneness of a cooked piece of meat, a meat testing fork and other surface-puncturing devices have been used to test the tenderness of meat by penetrating the meat. But tenderness of meat is not related to degrees of doneness of cooked meat. A piece of meat which is cooked to a rare degree can either be tough or tender, depending on the internal structure of that particular piece of meat, and the same rule applies to a piece of meat cooked to a medium rare, or medium well or well done degree of doneness. One current method of measuring the degree of doneness of meat is to cut it with a knife and observe the degree of doneness in the opening made by the knife. Several disadvantages of the penetration by knife or fork of a cooked piece of meat are the escaping of meat juices from the meat, the unevenness of cooking when heat escapes from the holes left by the knife or fork, and the relative unattractiveness of the surface-damaged cooked piece of meat when served to the consumer.

The prior art possibly related to this invention includes a device for testing the compression of flexible foam material but this compression testing device was never intended to be used on cooked meats or in any cooking method, nor did its inventor ever anticipate that a piece of meat undergoes a predetermined change in compressibility as it is being cooked.

The prior art possibly related to this invention also includes a gage for measuring the softness or texture resistance of a bakery product, especially bread. Softness means tenderness, which is desired by the majority of consumers. This device, which is used to determine the tenderness and internal texture or structure of bread, is not related to the present invention which measures the degree of doneness of cooked meat.

PRIOR ART STATEMENT

A search in the U.S. Patent Office has produced the following U.S. patents, which, in the applicant's opinion, are the closest prior art to this invention: U.S. Pat. Nos. 2,296,815; 2,446,956; 2,913,899; 2,975,631; 3,308,654; 3,564,735; 3,593,572; 3,696,662; 3,872,716; and 4,007,632. A review of these patents does not disclose the present invention.

SUMMARY OF THE INVENTION

The present invention is directed to a device and a kit and a method for measuring the degree of doneness of a cooked piece of meat, especially beef. As a piece of meat is being cooked from raw meat to well done meat, its ability to withstand external compression increases in a predictable manner. A piece of meat that is cooked to a certain standard degree of doneness will always have the same amount of compressibility for that certain standard degree of doneness. A resilient material, such as a flexible cellular foam material, including foam rubber, polyurethane foam, polyester foam, and polyether foam, can be made to have a known, predetermined, calibrated, distinct density and a related indentation load deflection value. The indentation load deflection value is obtained, according to an American Society for Testing and Materials test, by measuring the weight in pounds that is required to compress by 25%, a block of cellular foam material 54"×54"×4". We can refer to it as an ILD value.

In the present invention, blocks of flexible cellular foam material have been made to have known, predetermined, calibrated, distinct densities and related ILD values, so that the amount of compressibility of these blocks of material are equal to the amounts of compressibility of pieces of meat that have been cooked to certain standard degrees of doneness.

In a preferred embodiment of the present invention, four blocks of flexible cellular foam material are prepared, each block having an ILD value and an amount of compressibility which is equal to the amount of compressibility of a piece of meat which has been cooked to a certain known standard degree of doneness. For example, one block of flexible cellular foam material has been made with a density and ILD value that has the same amount of compressibility of a piece of meat that has been cooked to a standard rare degree of doneness. That block has been labeled "rare." A second block of flexible cellular foam material has been made with a density and ILD value that has the same amount of compressibility of a piece of meat that has been cooked to a standard medium rare degree of doneness. That second block has been labeled "medium rare." A third block of flexible cellular foam material has been made with a density and ILD value that has the same amount of compressibility of a piece of meat that has been cooked to a standard medium well degree of doneness. That third block has been labeled "medium well." A fourth block of flexible cellular foam material has been made with a density and ILD value that has the same amount of compressibility of a piece of meat that has been cooked to a standard well done degree of doneness. That fourth block has been labeled "well done."

The following densities in pounds per cubic inch and indentation load deflection values in pounds for flexible cellular foam materials have been determined to be equal to corresponding densities and ILD values for cooked meat which has been cooked to one of the four following standard degrees of doneness: (1) rare, (2) medium rare, (3) medium well done, and (4) well done.

|  | rare | medium rare | medium well | well done |
|---|---|---|---|---|
| density in lbs. per cubic inch | 1.8 | 2.2 | 2.5 | 7 to 8 |
| indentation load deflection value in lbs. | 32 to 44 | 50 to 58 | 62 to 80 | 92 to 102 |
| preferred ILD | 36 | 54 | 68 | 97 |

In a preferred embodiment of this invention, the four blocks, respectively labeled rare, medium rare, medium well, and well done, are arrayed on a tray, for use near the cooked piece of meat, whose degree of doneness is to be measured. The tray has four wells with each block resting in one of those wells. The tray has a fifth well, to hold a stick with a blunt end for compressing the cooked piece of meat, whose degree of doneness is to be measured and also for compressing the blocks of flexible cellular material to determine which block has an amount of compressibility which is equal to the amount of compressibility of the cooked piece of meat being measured for its degree of doneness. These blocks can have dimensions which will allow them to be placed and used efficiently in the area where meat is being cooked. In a preferred embodiment, each block is 3" long, 1¼" wide, and 1" thick, and is positioned in its own well, whose dimensions will be 4" × 2" × ½" deep.

To measure the degree of doneness of a cooked piece of meat, that cooked piece of meat is compressed, preferably by the blunt end of the stick which rests in a well on the tray. The four blocks of flexible cellular material are then compressed, preferably by the same blunt end of the stick, although the blunt end of any kitchen utensil handle or even a human finger can be used to compress either or both the meat and the blocks. The label, either rare, medium rare, medium well, or well done, of the block having the same amount of compressibility of the cooked piece of meat being measured for its degree of doneness, will describe the same degree of doneness as that cooked piece of meat.

If a chef or other cook wants a piece of meat of a particular degree of doneness, the chef can compare the amounts of compressibility of the cooked piece of meat with the blocks of flexible cellular foam material, and thus observe the degrees of doneness of the piece of meat as its doneness goes through the range of cooking from raw to the degree of doneness desired by the chef or other cook.

BRIEF DESCRIPTION OF THE DRAWING FIGURES

FIG. 1 is an isometric view not drawn to scale of a preferred embodiment of the invention, showing four blocks of flexible cellular material, each in its own well on a tray. Each block is labeled for a different standard degree of doneness. Each block has a different color for easy visual recognition. The tray also has a stick that rests in its own well.

DETAILED DESCRIPTION OF THE PREFERRED EMBODIMENT

Figure 1:
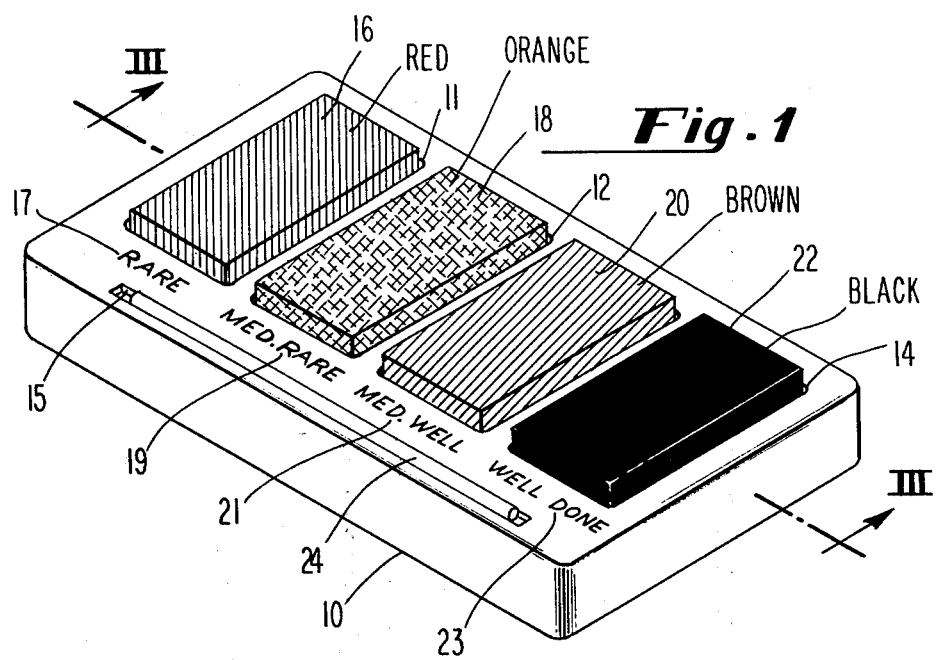
Figure 2:
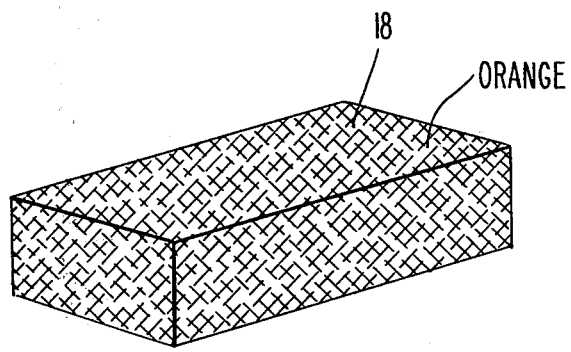
FIG. 2 is an isometric view not drawn to scale of an orange-colored block of flexible cellular material which has the same amount of compressibility as a piece of meat which has the same amount of compressibility as a piece of meat which has been cooked to a medium rare degree of doneness.
Figure 3:
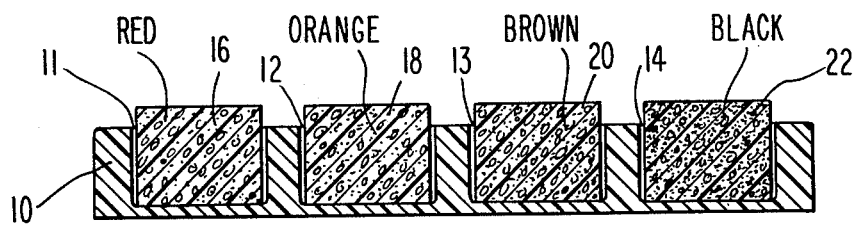
FIG. 3 is a vertical sectional view not drawn to scale taken along the line III—III of FIG. 1. It shows four blocks positioned in their respective wells in a tray.

Reference is now made to FIG. 1, which is an isometric view of the preferred embodiment of the invention. FIG. 1 is not drawn to scale. The tray 10 can be made of metal or plastic or other suitable material. In the preferred embodiment, tray 10 is 13" long, 7" wide and 1" deep. Tray 10 has four wells, 11, 12, 13, and 14, which are arrayed on the tray from the left side of the tray to the right side of the tray, one inch apart from each other. In the preferred embodiment, wells 11, 12, 13, and 14, are of equal dimensions, four inches long, two inches wide and one-half inch deep. Tray 10 also has a fifth well 15, which is nine inches long, one-half inch wide and one half inch deep.

Well 11 contains a block 16 of flexible cellular foam material, preferably slab polyester foam material, which has a density of 1.8 pounds per cubic inch and an ILD value between thirty-two and forty-four pounds, preferably thirty-six pounds. Block 16 has an amount of compressibility which is equal to the amount of compressibility of a piece of meat which has been cooked to a standard rare degree of doneness. Block 16 is colored red. The standard degree of doneness RARE 17 is printed next to block 16 on tray 10 between well 11 and well 15.

Well 12 contains a block 18 of flexible cellular foam material, preferably slab polyester foam material, which has a density of 2.2 pounds per cubic inch and an ILD value between fifty and fifty-eight pounds, preferably fifty-four pounds. Block 18 has an amount of compressibility which is equal to the amount of compressibility of a piece of meat which has been cooked to a standard medium rare degree of doneness. Block 18 is colored orange. The standard degree of doneness MEDIUM RARE 19 is printed next to block 18 on tray 10 between well 12 and well 15.

Well 13 contains a block 20 of flexible cellular foam material, preferably slab polyester foam material, which has a density of 2.5 pounds per cubic inch and an ILD value between sixty-two and eighty pounds, preferably fifty-eight pounds. Block 20 has an amount of compressibility which is equal to the amount of compressibility of a piece of meat which has been cooked to a standard medium well done degree of doneness. Block 20 is colored brown. The standard degree of doneness MEDIUM WELL 21 is printed next to block 20 on tray 10 between well 13 and well 15.

Well 14 contains a block 22 of flexible cellular foam material, preferably slab polyester foam material, which has a density of seven to eight pounds per cubic inch and an ILD value between ninety-two and one hundred and two pounds, preferably ninety-seven pounds. Block 22 has an amount of compressibility which is equal to the amount of compressibility of a piece of meat which has been cooked to a standard well done degree of doneness. Block 22 is colored black. The standard degree of doneness WELL DONE 23 is printed next to block 22 on tray 10 between well 14 and well 15.

Well 15 contains a stick 24, having at least one blunt end for compressing blocks 16, 18, 20 and 22 and for compressing a cooked piece of meat whose degree of doneness is being measured and for comparing the amounts of compressibility of blocks 16, 18, 20, and 22 with the amount of compressibility of that cooked piece of meat, to determine which block has the same amount of compressibility as that of the cooked piece of meat. The printed standard degree of doneness next to the block having an amount of compressibility equal to that of the cooked piece of meat will be the same standard degree of doneness as that of the cooked piece of meat. Stick 24 can be made of metal or other suitable material which is impervious to food flavors, juices and food contamination.

Having described my invention by reference to a preferred embodiment, I claim:

1. A device for measuring the degree of doneness of a cooked piece of meat comprising:

a plurality of blocks of resilient material, each of said blocks having a known, predetermined, calibrated distinct amount of compressibility, said amount of compressibility of each of said blocks being equal to a corresponding amount of compressibility of a model piece of meat which has been cooked to a known standard degree of doneness, each of said blocks having an exposed surface which is adapted to be compressed for measurement of the amount of compressibility thereof, the differences in compressibility between the plurality of blocks being pre-selected to represent a range in degrees of doneness of a cooked piece of meat.

2. A device for measuring the degree of doneness of a cooked piece of beef comprising:

a plurality of blocks of resilient material, each of said blocks having a known, predetermined, calibrated, distinct amount of compressibility, said amount of compressibility of each of said blocks being equal to a corresponding amount of compressibility of a model piece of beef which has been cooked to a known standard degree of doneness, each of said blocks having an exposed surface which is adapted to be compressed for measurement of the amount of compressibility thereof, the differences in compressibility between the plurality of blocks being pre-selected to represent a range in degrees of doneness of a cooked piece of beef.

3. A device as recited in claim 2 wherein said range in degrees of doneness of said cooked piece of beef comprises rare, medium rare, medium well done and well done degrees of doneness.

4. A device as recited in claim 2, wherein said plurality of blocks of resilient material comprises:

four blocks of resilient material, each of said blocks having a known, predetermined, calibrated, distinct amount of compressibility; said amount of compressibility of the first block being equal to a corresponding amount of compressibility of a model piece of beef which has been cooked to a standard rare degree of doneness, said amount of compressibility of the second block being equal to a corresponding amount of compressibility of a model piece of beef which has been cooked to a standard medium rare degree of doneness, said amount of compressibility of the third block being equal to a corresponding amount of compressibility of a model piece of beef which has been cooked to a standard medium well degree of doneness, said amount of compressibility of the fourth block being equal to a corresponding amount of compressibility of a model piece of beef which has been cooked to a standard well done degree of doneness.

5. A device as recited in claim 4, wherein said resilient material comprises flexible cellular foam material.

6. A device as recited in claim 5 wherein each said block has a color which is different from the color of each of the other said blocks.

7. A device as recited in claim 4 wherein said first block is colored red, said second block is colored orange, said third block is colored brown, and said fourth block is colored black.

8. A kit for measuring the degree of doneness of a cooked piece of meat comprising:

a plurality of blocks of resilient material, each of said blocks having a known, predetermined, calibrated, distinct amount of compressibility, said amount of compressibility of each of said blocks being equal to a corresponding amount of compressibility of a model piece of meat which has been cooked to a known standard degree of doneness, each of said blocks having an exposed surface which is adapted to be compressed for measurement of the amount of compressibility thereof, the differences in compressibility between the plurality of blocks being pre-selected to represent a range in degrees of doneness of a cooked piece of meat, means for compressing each of said blocks; and a tray having a plurality of wells, said wells being arrayed in proximity with each other, each well of said plurality of wells containing one of said blocks of resilient material, each said well being of a size larger than said block contained in said well, thus allowing said block to expand without contacting a side of said well when said block is compressed on said exposed surface.

9. A kit, as recited in claim 7, wherein a first block has the word RARE printed next to it, a second block has the words MED. RARE printed next to it, a third block has the words MED. WELL printed next to it, and a fourth block has the words WELL DONE printed next to it.

10. A kit, as recited in claim 8 wherein said compressing means comprises a stick with at least one blunt end.

11. A kit as recited in claim 8 wherein said resilient material comprises flexible, cellular foam material.

12. A method of measuring the degree of doneness of a cooked piece of meat comprising the steps of:

(1) Compressing an exposed surface of said cooked piece of meat, to determine the amount of compressibility of said cooked piece of meat, (2) compressing a plurality of blocks of resilient material, each of said blocks having a known, predetermined, calibrated, distinct amount of compressibility of a model cooked piece of meat which has been cooked to a known standard degree of doneness, (3) comparing the amount of compressibility of said cooked piece of meat with the amount of compressibility of each of said blocks, (4) determining which is equal to the amount of compressibility of said cooked piece of meat, (5) equating the amount of compressibility of said cooked piece of meat with the amount of compressibility of said one of said blocks, (6) relating said one of said blocks to a model cooked piece of meat, whose amount of compressibility is equal to the amount of compressibility of said one of said blocks, and (7) determining the known standard degree of doneness of said model cooked piece of meat, whose degree of doneness is equal to the degree of doneness of said cooked piece of meat.

* * * * *

UNITED STATES PATENT AND TRADEMARK OFFICE
CERTIFICATE OF CORRECTION

PATENT NO. : 4,141,239

DATED : February 27, 1979

INVENTOR(S) : John Gilbert

It is certified that error appears in the above-identified patent and that said Letters Patent are hereby corrected as shown below:

Column 3, lines 37-40, "orange -colored block of flexible material which has the same amount of compressibility as a piece meat which has the same amount of compressiblity as a piece of meat which has been cooked to a medium rare" should read ---orange-colored block of flexible cellular material which has the same amount of compressibility as a piece of meat which has been cooked to a rear medium ---.

Column 4, line 19 "fifty-eight pounds. Block 20 has an amount of compress-" should read --sixty-eight pounds. Block 20 has an amount of compress- --.

Signed and Sealed this

Seventeenth Day of July 1979

[SEAL]

Attest:

Attesting Officer

LUTRELLE F. PARKER
*Acting Commissioner of Patents and Trademarks*